(12) United States Patent
Park et al.

(10) Patent No.: US 8,744,803 B2
(45) Date of Patent: Jun. 3, 2014

(54) METHODS, SYSTEMS AND DEVICES FOR ACTIVITY TRACKING DEVICE DATA SYNCHRONIZATION WITH COMPUTING DEVICES

(71) Applicant: Fitbit, Inc., San Francisco, CA (US)

(72) Inventors: James Park, Berkeley, CA (US); Barry Burton, San Francisco, CA (US); Heiko Panther, Oakland, CA (US); Eric Friedman, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/050,292

(22) Filed: Oct. 9, 2013

(65) Prior Publication Data

US 2014/0039804 A1   Feb. 6, 2014

Related U.S. Application Data

(60) Continuation-in-part of application No. 13/959,714, filed on Aug. 5, 2013, which is a continuation-in-part of application No. 13/693,334, filed on Dec. 4, 2012, now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, said application No. 13/959,714 is a continuation-in-part of application No. 13/759,485, filed on Feb. 5, 2013, now Pat. No. 8,543,351, which is a division of application No. 13/667,229, which is a division of application No. 13/469,027, which is a division of application No. 13/246,843, which is a division of application No. 13/156,304, application No. 14/050,292, which is a continuation-in-part of application No. 13/872,015, filed on Apr. 26, 2013.

(60) Provisional application No. 61/388,595, filed on Sep. 30, 2010, provisional application No. 61/390,811, filed on Oct. 7, 2010, provisional application No. 61/638,650, filed on Apr. 26, 2012.

(51) Int. Cl.
*G06F 19/00* (2011.01)
*G11B 27/10* (2006.01)

(52) U.S. Cl.
CPC .................................. *G11B 27/105* (2013.01)
USPC ......................................................... 702/160

(58) Field of Classification Search
CPC ........... G11B 2220/216; G11B 27/105; G11B 27/034; H04N 9/8042; H04N 9/8063
USPC .......................... 702/160, 155, 150, 182–185
See application file for complete search history.

(56) References Cited

U.S. PATENT DOCUMENTS 6,085,248 A * 7/2000 Sambamurthy et al. ...... 709/229

*Primary Examiner* — Edward Raymond
(74) *Attorney, Agent, or Firm* — Martine Penilla Group, LLP

(57) ABSTRACT

Methods, systems and devices are provided for capturing activity data associated with activity of a user via a device and transferring the data to a client device at a selected defined transfer rate, based on an update condition. The activity data is captured over time. The activity data is stored in storage of the device. The method sets a data transfer rate between the device and the computing device based upon the detected update condition. The update condition is used to select one of a first transfer rate for transferring activity data captured and stored over a period of time or a second transfer rate for transferring activity data that is displayable in substantial-real time on the computing device. The first transfer rate is set in response to scaling-up a connection interval and the second transfer rate is set in response to scaling-down the connection interval.

30 Claims, 10 Drawing Sheets

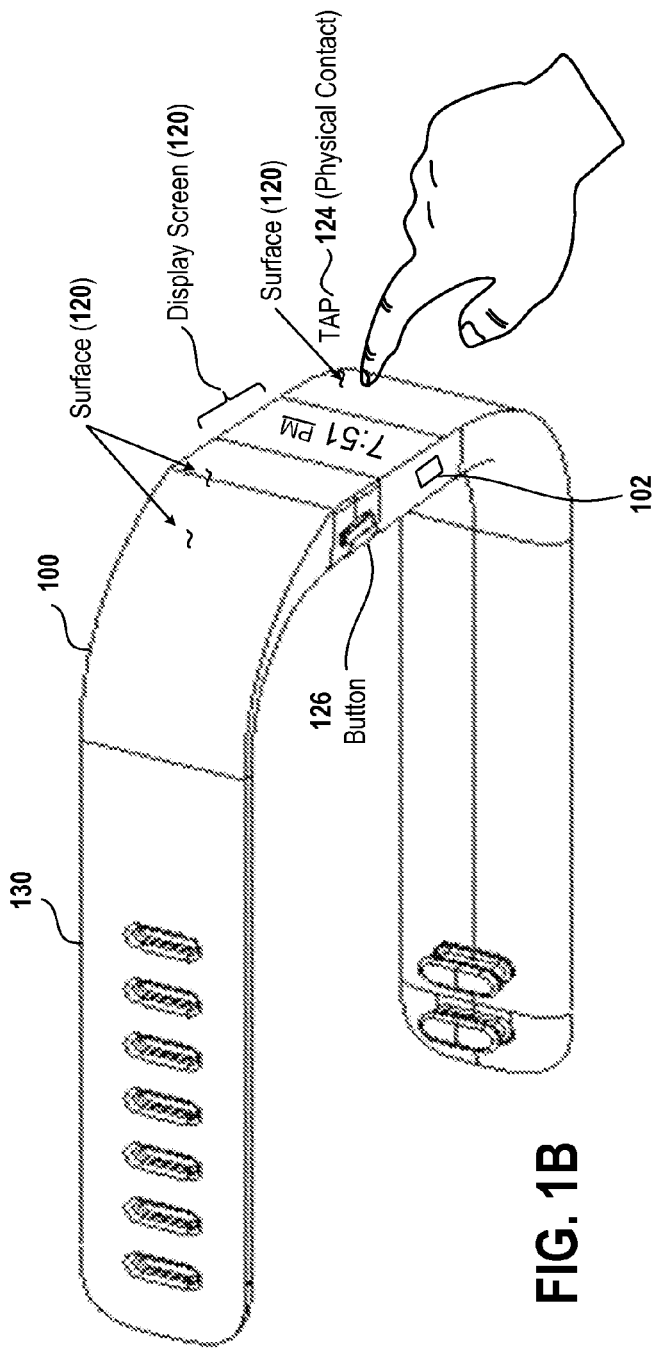
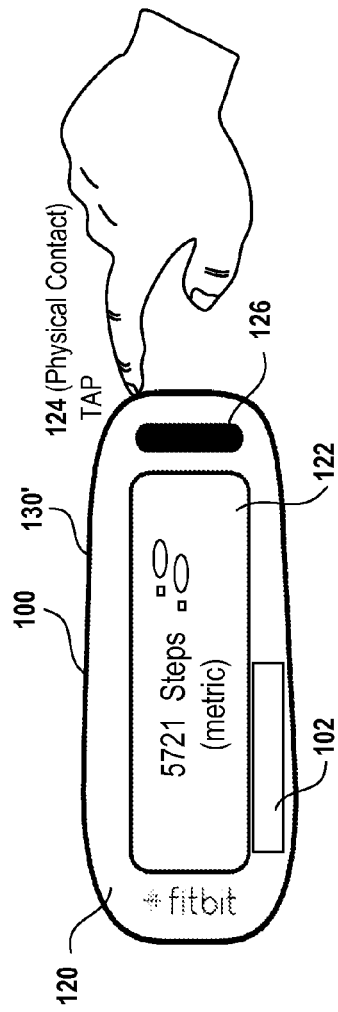
FIG. 1B
FIG. 1C

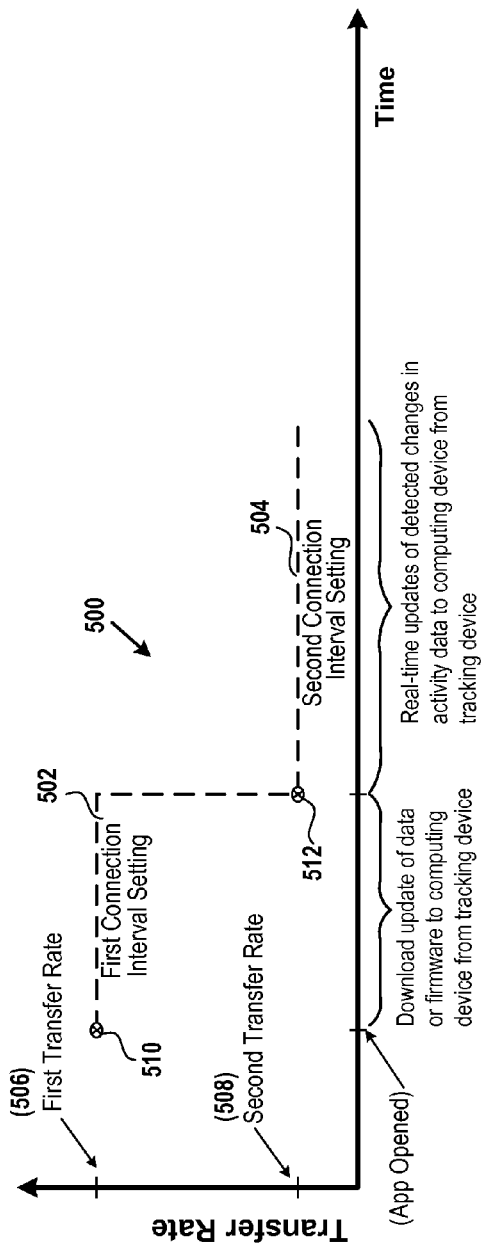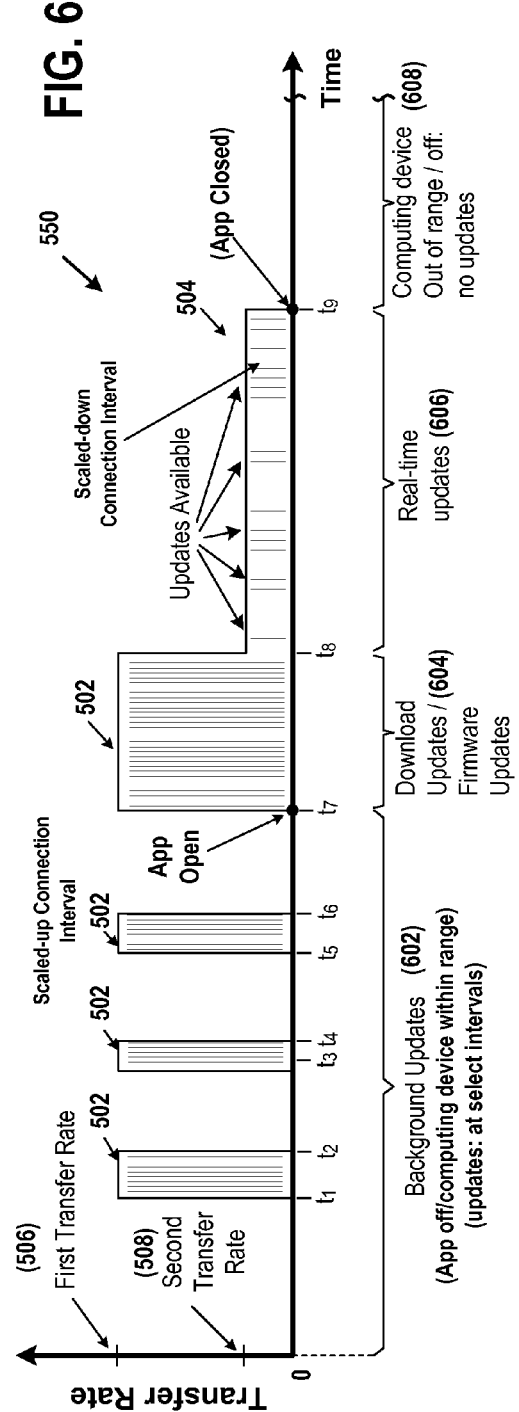

METHODS, SYSTEMS AND DEVICES FOR ACTIVITY TRACKING DEVICE DATA SYNCHRONIZATION WITH COMPUTING DEVICES

CLAIM OF PRIORITY

This application claims priority to U.S. Provisional Patent Application No. 61/885,962, filed on Oct. 2, 2013, entitled "Methods, Systems and Devices for Activity Tracking Device Data Synchronization with Computing Devices", which is herein incorporated by reference.

This application is a continuation-in-part of U.S. patent application Ser. No. 13/959,714, filed on Aug. 5, 2013, titled "Methods and Systems for Identification of Event Data Having Combined Activity and Location Information of Portable Monitoring Devices", which is a continuation-in-part of U.S. patent application Ser. No. 13/693,334 (now issued as U.S. Pat. No. 8,548,770, issued on Oct. 1, 2013), filed on Dec. 4, 2012, titled "Portable Monitoring Devices and Methods for Operating Same", which is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same", and to U.S. Provisional Patent Application No. 61/390,811, filed on Oct. 7, 2010, and titled "Portable Monitoring Devices and Methods for Operating Same", all of which are hereby incorporated by reference in their entirety, except for U.S. patent application Ser. No. 13/959,714.

This application is a continuation-in-part of Ser. No. 13/959,714, filed Aug. 5, 2013, titled "Methods and Systems for Identification of Event Data Having Combined Activity and Location Information of Portable Monitoring Devices", which is a continuation-in-part of U.S. patent application Ser. No. 13/759,485, (now issued as U.S. Pat. No. 8,543,351, issued on Sep. 24, 2013), filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety, except for U.S. patent application Ser. No. 13/959,714.

This application is a continuation-in-part of U.S. patent application Ser. No. 13/872,015, filed on Apr. 26, 2013, entitled "Secure Pairing of Devices via Paring Facilitator-Intermediary Device," which claims priority from U.S. Provisional Patent Application No. 61/638,650, filed on Apr. 26, 2012, both of which are herein incorporated by reference.

CROSS REFERENCE TO RELATED APPLICATION

This Application is related to U.S. application Ser. No. 14/050,301, filed on Oct. 9, 2013, entitled "Methods, Systems, and Devices for Generating Real-Time Activity Data Updates to Display Devices," which claims priority to U.S. Provisional Application No. 61/885,966, filed on Oct. 2, 2013, both of which are incorporated herein by reference.

FIELD

The present disclosure relates to systems and methods for capturing activity data over a period of time and synchronizing data transfers between a tracker device and a client device.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces. In addition, updates between a tracker and a client device usually require wired connectors and/or complex syncing schemes.

It is in this context that embodiments described herein arise.

SUMMARY

Embodiments described in the present disclosure provide systems, apparatus, computer readable media, and methods for setting a data transfer rate between an activity tracking device and a computing device client, based on a detected update condition. The transfer rates are set by scaling the connection interval of data transfers up or down, depending on the type/amount of data to be transferred in accordance with the update condition.

In one embodiment, a method is provided. The method includes capturing activity data associated with activity of a user via a device. The activity data is captured over time, and the activity data is quantified by a plurality of metrics. The method acts to store the activity data in storage of the device and connecting the device with a computing device over a wireless communication link. The method detects an update condition when the device is connected with the computing device. The method sets a data transfer rate between the device and the computing device based upon the detected update condition. The update condition is used to select one of a first transfer rate for transferring activity data captured and stored over a period of time or a second transfer rate for transferring activity data that is displayable in substantial-real time on the computing device. The update condition is used to select the first transfer rate when an activity tracking application is detected to be opened on the computing device, and the update condition is used to select the second transfer rate while the device is connectable with the computing device and the activity tracking application remains open, the method is executed by a processor.

In another embodiment, a device configured for capture of activity for a user is provided. The device includes a housing and a sensor disposed in the housing to capture activity data associated with activity of the user. The activity data is captured over time, and the activity data is quantified by a plurality of metrics associated. A memory for storing the captured activity data is provided in the device. The device further includes a processor for connecting the device with a computing device over a wireless communication link. The processor detects an update condition when the device is connected with the computing device, such that the processor sets a data transfer rate between the device and the computing device based upon the detected update condition. The update condition used to select one of a first transfer rate for transferring activity data captured and stored over a period of time or a second transfer rate for transferring activity data for display in substantial-real time on the computing device. The update condition is used to select the first transfer rate when an activity tracking application on the computing device is detected to be open, and used to select the second transfer rate while the device is connectable with the computing device and the activity tracking application remains open.

In another embodiment, a method is provided. The method includes capturing activity data associated with activity of a user via a device. The activity data is captured over time, and the activity data quantified by a plurality of metrics. The activity data is stored in storage of the device. The method includes connecting the device to a computing device over a wireless communication link and detecting an update condition. The method sets a data transfer rate between the device and the computing device based upon the detected update condition. The update condition is used to select one of a first transfer rate for transferring activity data captured and stored over a period of time or a second transfer rate for transferring activity data that is displayable in substantial-real time on the computing device. The update condition is used to select the first transfer rate when starting an activity tracking application on the computing device is detected, and the update condition is further used to select the second transfer rate while the device is connected with the computing device and the activity tracking application is open. The method includes transferring the activity data from the device to the computing device at the selected first or second transfer rate. The first transfer rate is set in response to scaling-up a connection interval and the second transfer rate is set in response to scaling-down the connection interval, the method is executed by a processor.

Computer readable medium for storing program instructions executable by a processor, for managing the transfer of data between an activity tracking device and a computing device client is also provided.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings.

FIG. 1B illustrates an example of an activity tracking device, in accordance with one embodiment of the present invention.

FIG. 1C illustrates another example of an activity tracking device, in accordance with one embodiment of the present invention.

FIG. 5 is a diagram showing dynamic switching between first connection interval settings and second connection interval settings, in accordance with one embodiment of the present invention.

FIG. 6 illustrates a graph showing various periods of time when transfers may occur between the activity tracking device and the client device, in accordance with one embodiment of the present invention.

DETAILED DESCRIPTION

Figure 1A:
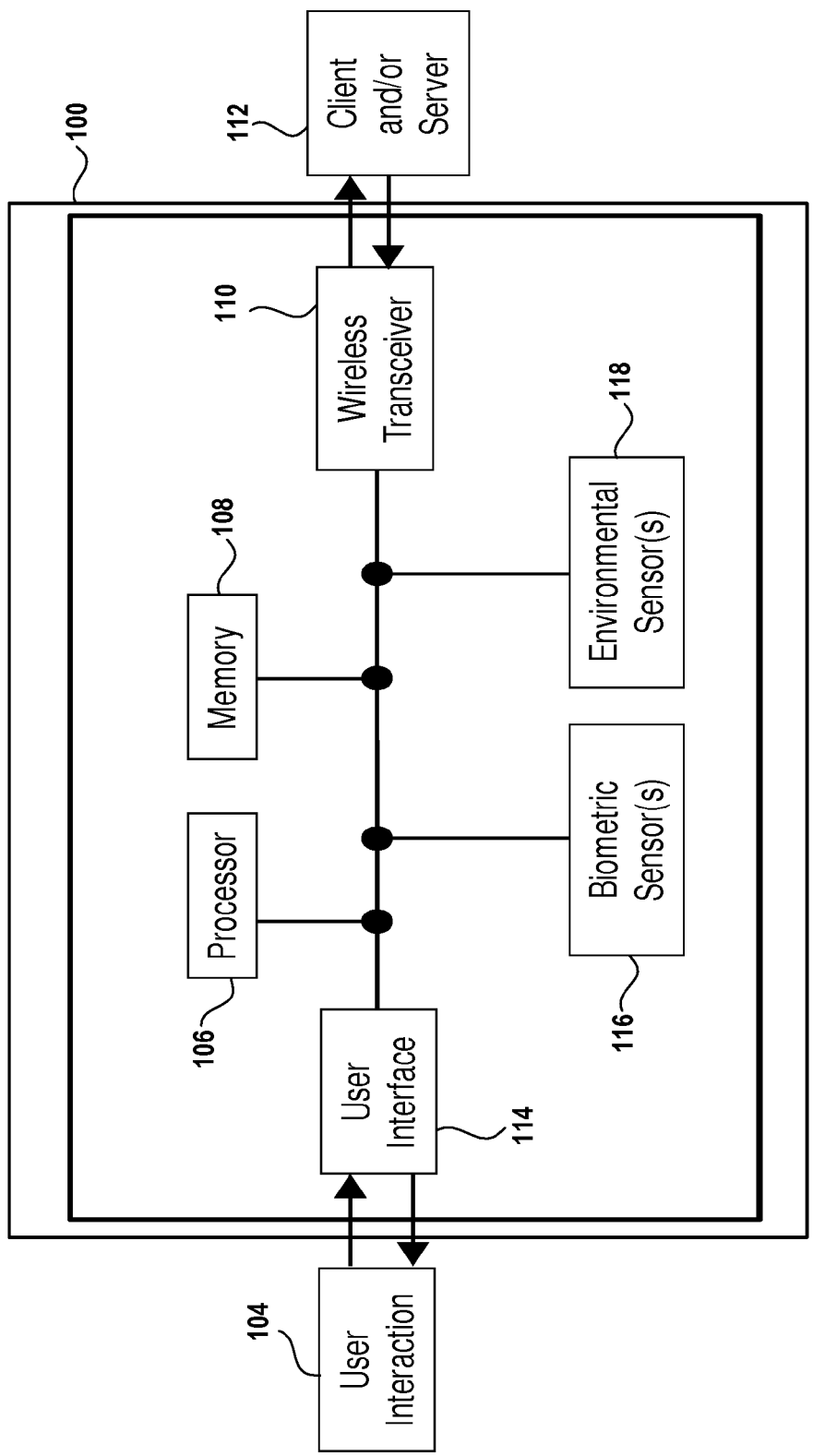
FIG. 1A shows a block diagram of an activity tracking device, in accordance with one embodiment of the present invention.

Embodiments described in the present disclosure provide systems, apparatus, computer readable media, and methods for scaling a connection interval for data transfers to and from an activity tracking device and a computing device. The computing device can be a computer that executes an activity tracking application (APP). The computing device can take on any form, so long as it can process information, load and execute an application, and can communicate wirelessly with the activity tracking device. For example purposes, the computing device can be a computer, a tablet computer, a smart phone, a tablet, a laptop, a desktop, a watch computer, glasses computer, or any device having access to memory and processing power.

The scaling of the connection interval enables dynamic setting of a data transfer rate between the activity tracking device and the computing device, based on a determined update condition. The update condition can include detecting that an application (e.g., activity tracking application) on the computing device has been opened, which causes a first transfer rate to be set. The first transfer rate has a scaled-up connection interval which allows for a higher frequency of packets to be sent between the activity tracking device and the computing device (e.g., changes the packet transfer frequency).

The scaled-up connection interval of the first transfer rate enables larger blocks of data and/or data logs to be downloaded faster from the activity tracking device to the computing device, so as to enable display of tracked or monitored information collected when the application was not open or the computing device was not in wireless connection range with the activity tracking device. In some embodiments, the scaled-up connection interval also enables transfer of data for firmware updates of the device, when updates are needed, scheduled or required. In one configuration, if the update conditions dictate that the activity tracking device is generating data that can be transferred to the computing device, while the application is open, the connection interval can be scaled-down to set a second data transfer rate between the activity tracking device and the computing device. In one embodiment, during the first transfer rate, the transfer of data from the activity tracking device is set directly to the site, e.g., storage associated with a website that manages accounts concerning activity tracking information. In some embodiments, the computing device acts as a transfer pipe between the activity tracking device and the website.

The second transfer rate is used to transfer updates to enable definition of metrics regarding the monitored or captured activity data. In the scaled-down connection interval, the data transfer rate is slower than the scaled-up connection interval, but the amount of data to be transferred is typically less or is data that is just detected/monitored by the activity tracking device. Thus, the second transfer rate of the scaled-down connection interval is sufficient to enable transfer of updates for activity data captured, monitored, or collected by the activity tracking device to the computing device. The transfers of updates enable such activity data to be processed by the computing device and displayed in substantial real-time on a screen of the computing device, just as the activity is occurring and the connection between the activity tracking device and computing device can be maintained. In one embodiment, the second transfer rate is sufficient to enable an external device (e.g., computing device, smartphone, tablet, laptop, desktop, watch computer, glasses computer, etc.) to serve as a real time data display.

Furthermore, the transferred data need not be only motion data or activity data, but the data can include any type of data, such as altitude or relative altitude data, barometric pressure data, heart rate data, temperature data, alarm data, goal data, history status data, processed data, raw data, etc.

Additionally, although the computing device may usually have access to an Internet connection, every transfer between the activity tracking device and the computing device does not require Internet connection. When the computing device is connected to the Internet, the computing device can then sync data to a server. The server, in one embodiment, can be one or more distributed servers, data centers, virtualized servers in distributed data centers, etc. The server, in one embodiment, executes an activity management application that enables user account access to metrics associated with activity tracking devices.

It should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

FIG. 1A shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, tapping, sliding, rubbing, multiple taps, gestures, etc.).

In some embodiments, the user interface 114 is configured to receive user interaction 104 that is in the form of noncontact input. The noncontact input can be by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. As will be explained in more detail below, the physical contact may be in the form of a tap or multiple taps by a finger upon the housing of the activity tracking device 100.

FIG. 1B illustrates an example of an activity tracking device 100 having a housing 130 in the form of a wearable wrist attachable device. The sensors of the activity tracking device 100 can, as mentioned above, detect motion such as physical contact that is applied and received on a surface 120 of the housing 130. In the example shown, the physical contact 124 is in the form of a tap or multiple taps on the surface 120. Device components 102 are, in one embodiment, contained within the housing 130. The location at which the device components 102 are integrated into the housing 130 can vary. For example, the device components 102 can be integrated throughout various locations around the housing 130, and not limited to the central portion of the wrist attachable device. In some embodiments, the device components 102 can be integrated into or with a smart watch device.

In other embodiments, the device components 102 are positioned substantially in a central position of the wrist attachable device, such as under or proximate to a location where a display screen 122 is located. In the illustrated example, the housing 130 also includes a button 126. The button 126 can be pressed to activate the display screen 122, navigate to various metrics displayed on the screen 122, or turn off the screen 122.

FIG. 1C illustrates another example of an activity tracking device 100, in accordance with one embodiment of the present invention. The form factor of the activity tracking device 100 is shown as a clickable device that includes a screen 122, a button 126, and device components 102 integrated within the housing 130'. The housing 130' can include a clip that allows for attachment to clothing or articles of the user, or to simply place the device within a pocket or holder of the user. Accordingly, the physical contact 124 shown with respect to FIG. 1B can also be implemented upon the surface 120 of activity tracking device 100 of FIG. 1C. It should be understood, therefore, that the form factor of the activity tracking device 100 can take on various configurations and should not be limited to the example configurations provided herein.

Figure 2:
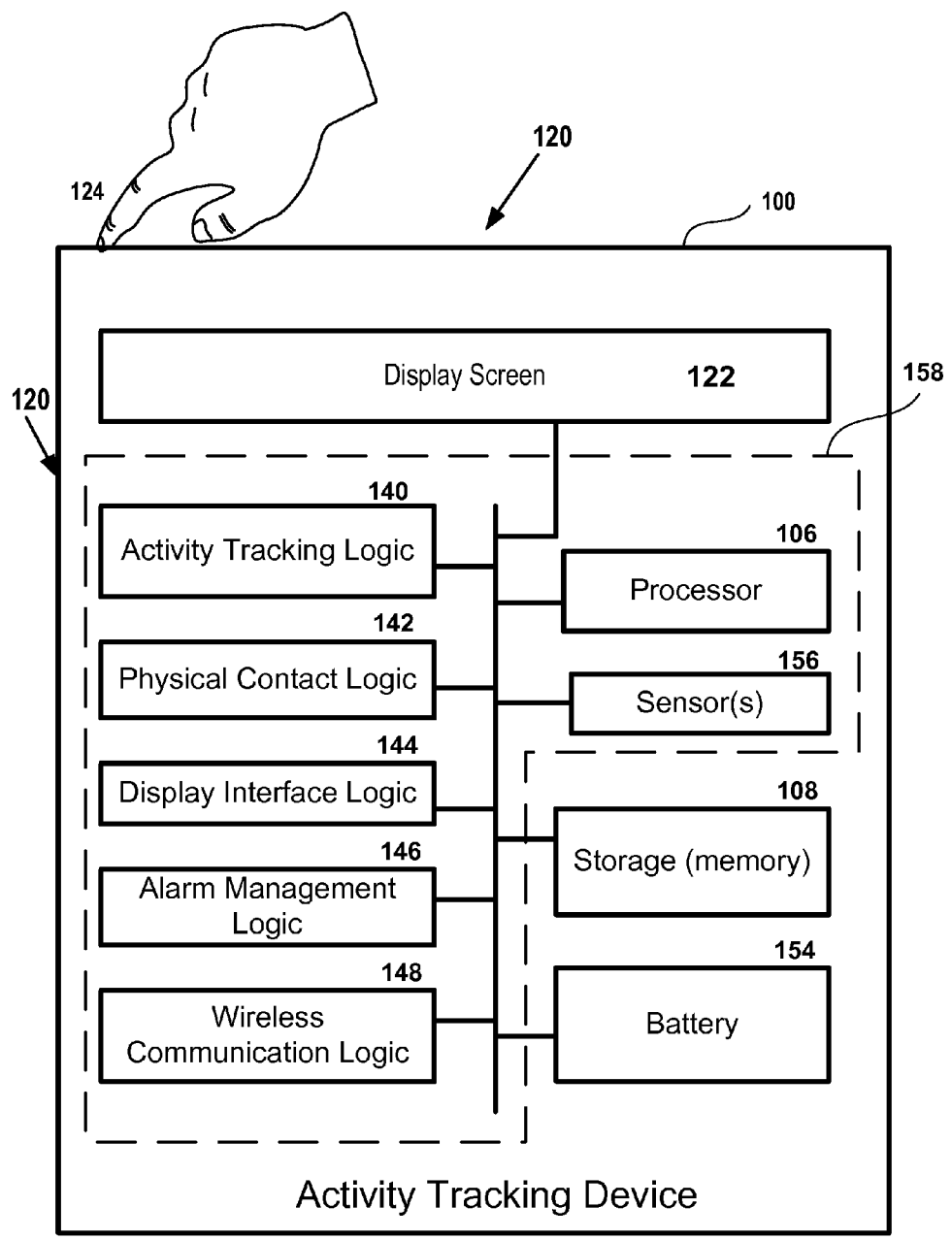
FIG. 2 illustrates an example of activity tracking device including example components utilized for tracking activity and motion of the device, and associated interfaces to a display screen, in accordance with one embodiment of the present invention.

FIG. 2 illustrates an example of activity tracking device 100 of FIG. 1A, showing some additional example components utilized for tracking activity and motion of the device, and associated interfaces to display screen 122. In this example, the finger of a user can be used to tap and provide physical contact 124 onto any surface 120 of activity tracking device 100. The physical contact, when sensed by sensors 156 of the activity tracking device 100, will cause a response by the activity tracking device 100, and therefore provide some metric on the display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 2, the activity tracking device 100 includes logic 158. Logic 158 may include activity tracking logic 140, physical contact logic 142, display interface logic 144, alarm management logic 146, wireless communication logic 148, processor 106, and sensors 156. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

In other embodiments, the physical contact logic can be programmed to determine when particular physical contacts occurred, the time in between the physical contacts, and whether the one or more physical contacts will qualify within predefined motion profiles that would indicate that an input is desired. If physical contact occurs that is not within some predefined profile or pattern, the physical contact logic will not indicate or qualify that physical contact as an input.

The display interface logic 144 is configured to interface with the processor and the physical contact logic to determine when specific metric data will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 3:
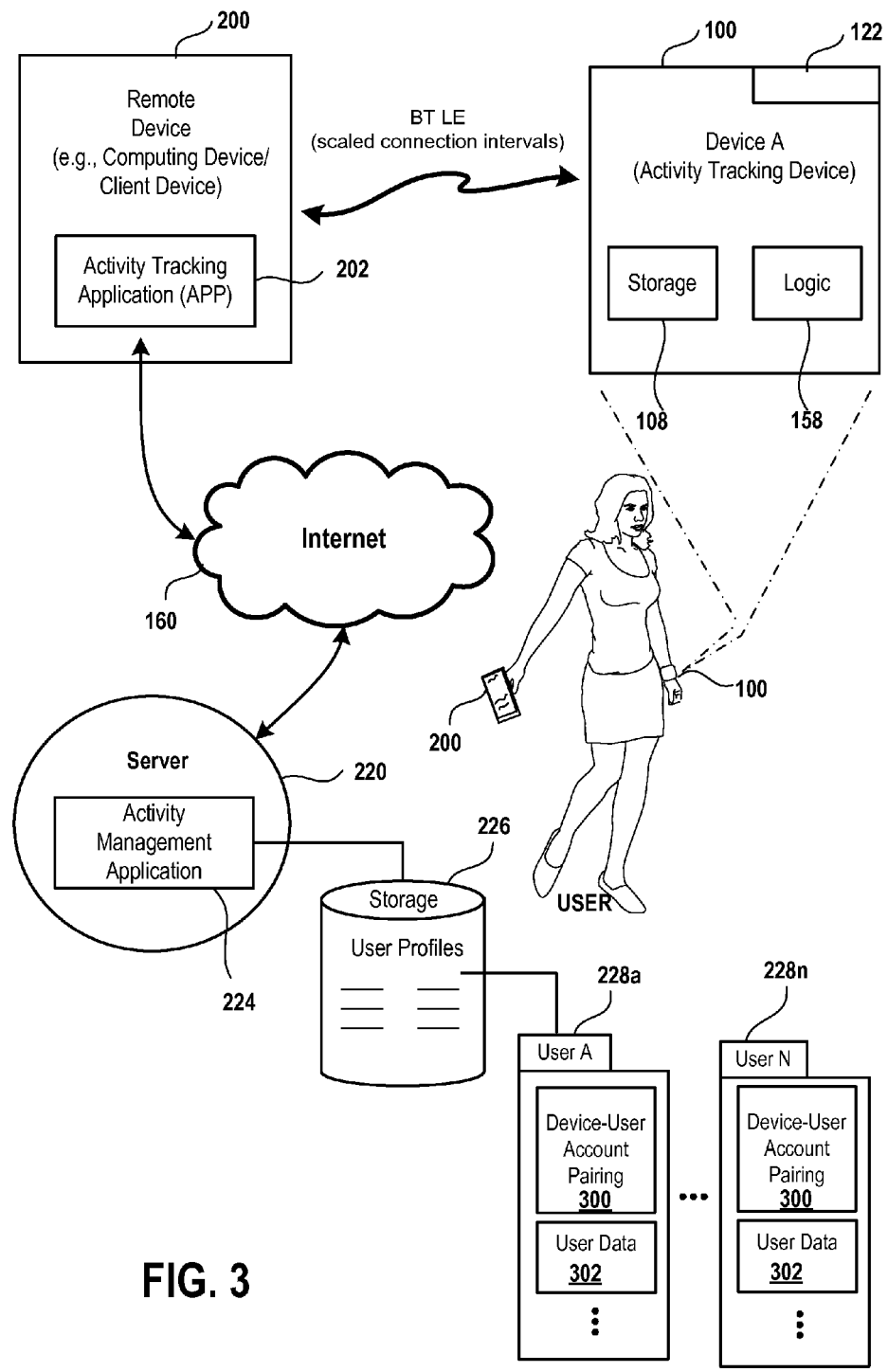
FIG. 3 illustrates an example of activity tracking device in communication with a remote device and interfaces with a server, in accordance with one embodiment of the present invention.

FIG. 3 illustrates an example of activity tracking device 100 in communication with a remote device 200. Remote device 200 is a computing device that is capable of communicating wirelessly with activity tracking device 100 and with the Internet 160. Remote device 200 can support installation and execution of applications (e.g., APPs, mobile APPs, etc.). Such applications can include an activity tracking application 202. Activity tracking application 202 can be downloaded from a server. The server can be a specialized server or a server that provides applications to devices, such as an application store. Once the activity tracking application 202 is installed in the remote device 200, the remote device 200 can communicate or be set to communicate with activity tracking device 100 (Device A). The remote device 200 can be a smartphone, a handheld computer, a tablet computer, a laptop computer, a desktop computer, or any other computing device capable of wirelessly interfacing with Device A. In one embodiment, the remote device can also have circuitry and logic for communicating with the Internet. However, it should be understood that an Internet connection is not required to enable the remote device 200 to communicate with the activity tracking device 100.

In one embodiment, remote device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Remote device 200 can also communicate with the Internet 160 using an Internet connection. The Internet connection of the remote device 200 can include cellular connections, wireless connections such as Wi-Fi, and combinations thereof (such as connections to switches between different types of connection links). The remote device, as mentioned above, can be a smartphone or tablet computer, or any other type of computing device having access to the Internet and with capabilities for communicating with the activity tracking device 100.

In one embodiment, a server 220 is also provided, which is interfaced with the Internet 160. The server 220 can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. Server 220 can include storage 226 that includes various user profiles associated with the various user accounts. The user account 228a for user A and the user account 228n for user N are shown to include various information.

The information can include, without limitation, device-user account paring 300, system configurations, user configurations, settings and data, etc. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user. In one embodiment, the server 220 provides access to a user to view the user data 302 associated with activity tracking device. The user data can include historical activity data.

The data viewable by the user includes the tracked motion data, which is processed to identify a plurality of metrics associated with the motion data. The metrics are shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

The configurations may include defining which metrics will be displayed on the activity tracking device 100. In addition, the configurations can include identification of which metrics will be a first metric to be displayed on the activity tracking device. The first metric to be displayed by the activity tracking device can be in response to a user input at the activity tracked device 100. As noted above, the user input can be by way of physical contact. The physical contact is qualified by the processor and/or logic of the activity tracking device 100 to determine if the physical contact should be treated as an input. The input can trigger or cause the display screen of the activity tracking device 100 to be turned on to display a specific metric, that is selected by the user as the first metric to display. In another embodiment, the first metric displayed in response to the input can be predefined by the system as a default.

The configuration provided by the user by way of the server 220 and the activity management application 224 can also be provided by way of the activity tracking application 202 of the computing device 200. For example, the activity tracking application 202 can include a plurality of screens that also display metrics associated with the captured motion data of the activity tracking device 100. The activity tracking application 202 can also allow for user input and configuration at various graphical user interface screens to set and define which input will produce display.

Figure 4A:
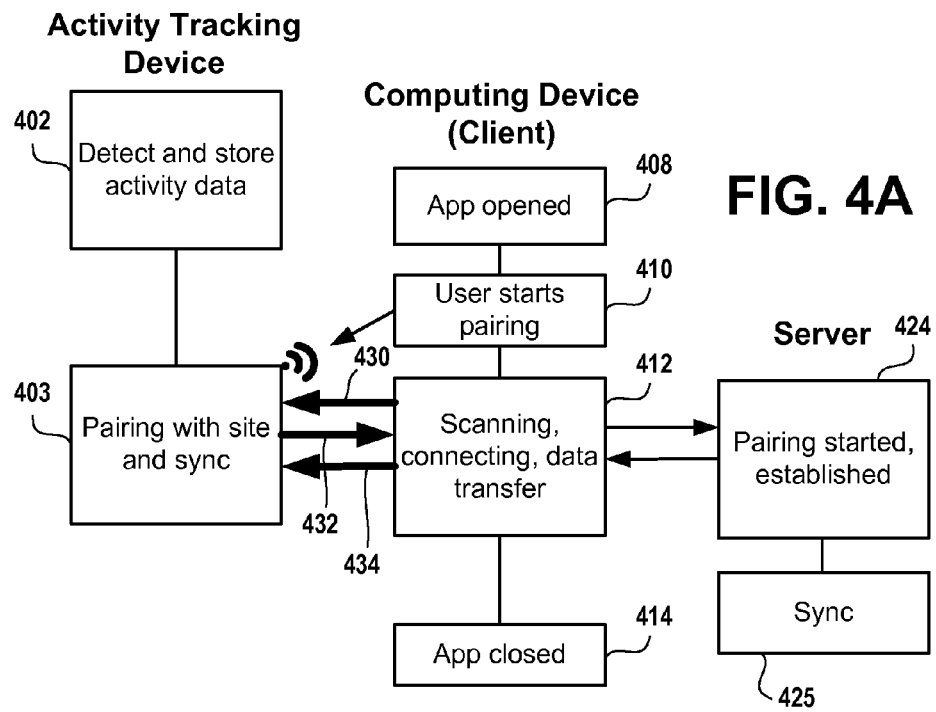
FIGS. 4A-4C illustrate embodiments for communication operations between an activity tracking device, a client device, and a backend server.
Figure 4B:
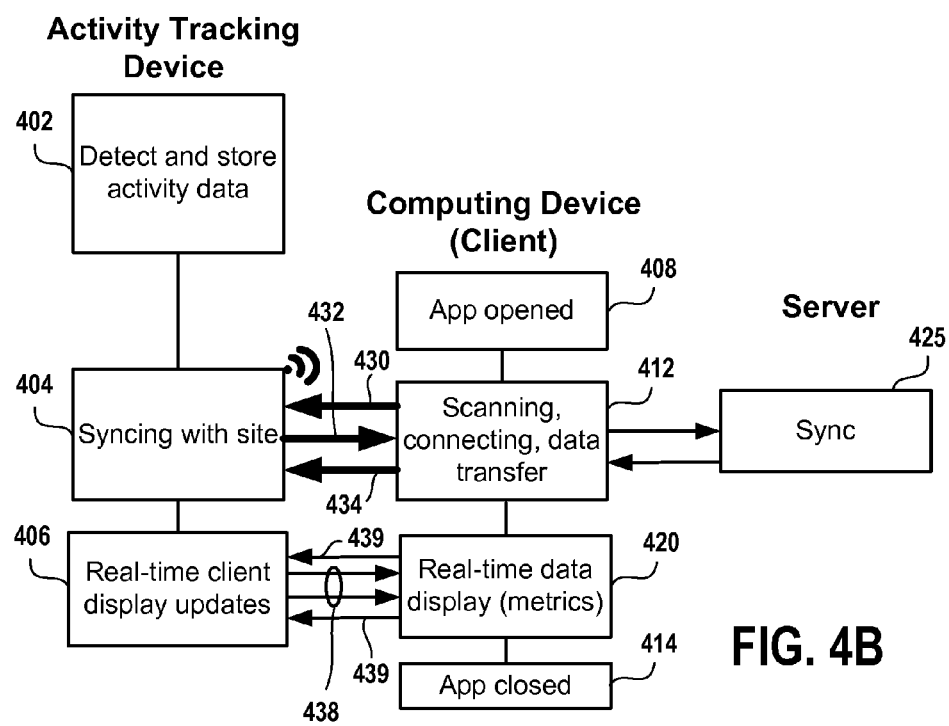
Figure 4C:
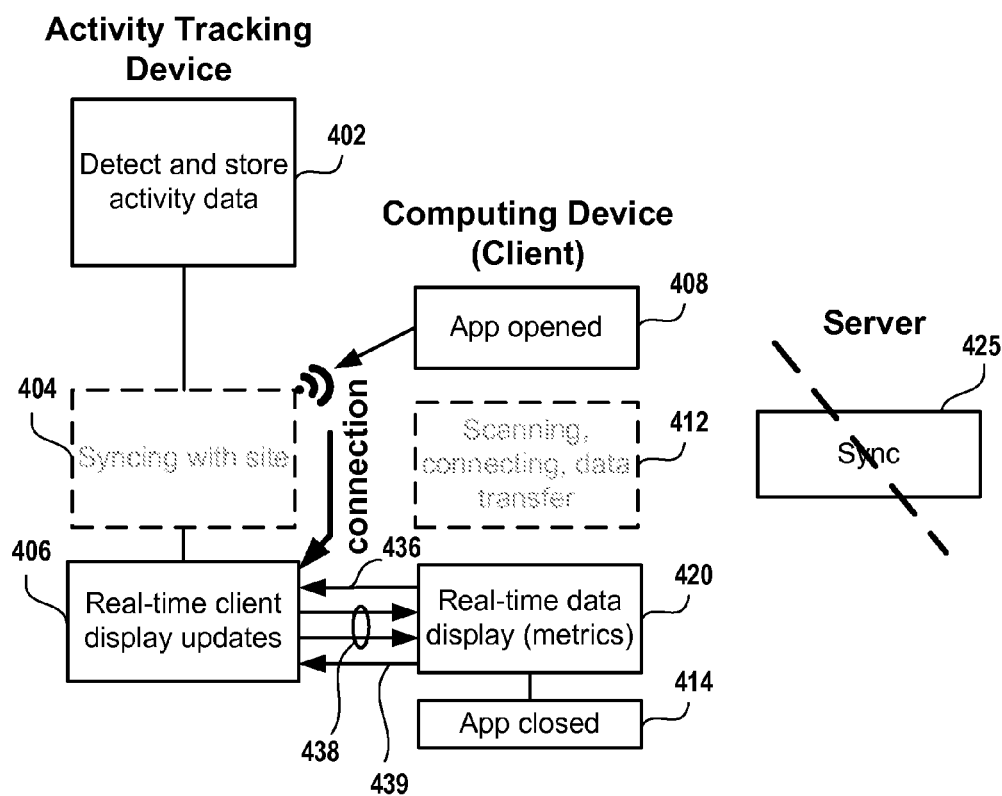

FIGS. 4A-4C illustrates embodiments of communication operations between an activity tracking device, a client device, and a backend server, in accordance with one embodiment of the present invention.

The communication described with reference to the flow diagrams in FIGS. 4A-4C should only be viewed as exemplary of operations that occur between the activity tracking device, a client device (computing device), and a backend server (server). In this illustrated example, thick pointed arrows indicate that a connection interval has been scaled up so as to operate data transfers at a first data transfer rate, while a thin pointed arrow indicates a connection interval that has been scaled down so as to operate data transfers at a second data transfer rate.

In one embodiment, the first transfer rate is designed to allow the transfer of larger amounts of data that have been stored on the activity tracking device over a period of time, such as since the last connection was made to a computing device. The activity tracking data stored on the activity tracking device can include, for example, motion data associated with the various activities performed by a user, data sensed by the activity tracking device, or data measured by the activity tracking device.

The various activities may include, without limitation, walking, running, jogging, walking up and down stairs, and general movement. Other information that can be stored by the activity tracking device can include, for example, measured information such as heart rate information, temperature information, etc. In one embodiment, storage of the activity tracking device will store this information for a period of time until a connection is made to a client device, such as a computing device configured to sync with the activity tracking device. In one embodiment, the computing device (client device) can be a smart phone, a tablet computer, a laptop computer, a desktop computer, or a general computing device.

In one embodiment, the first transfer rate is defined by scaling up the connection interval of the communication channel established between the activity tracking device and the client device. For example, if the communication channel is a low energy Bluetooth connection, the connection interval can be scaled to enable a transfer of packets that is more frequent than the second transfer rate.

First Transfer Rate (Connection Interval Scale-Up)

The connection interval for the first transfer rate can be scaled up to set a throughput of packets, such that each packet is transferred in less than about 200 milliseconds (ms). In one example embodiment, the first transfer rate is set to transfer one packet every about 10 ms to about 30 ms. In another example embodiment, the first transfer rate can be one packet every about 20 ms. In one embodiment, each packet is about 20 bytes.

In one embodiment, the first data transfer rate may be defined in terms of a frequency, in a range of between about 500 Bps (bytes per second) and about 2 kBps (kilobytes per second). In one example data transfer rate is about 1 kBps (kilobyte per second).

Second Transfer Rate (Connection Interval Scale-Down)

The connection interval for the second transfer rate can scaled down to set a throughput of packets, such that each packet is transferred at an interval that is greater than about 200 milliseconds (ms). In one example embodiment, the second transfer rate is set to transfer a packet every 500 ms. In some embodiments, depending on the frequency of events or lack of events, the transfer rate can be set to update only after several seconds (e.g., about 1-10 seconds). In one embodiment, each packet is about 20 bytes.

In one embodiment, the second data transfer rate may define a frequency value that is less than 500 bps (bytes per second). In another embodiment, the second data transfer rate can be set to a value that is less than 100 bps (bytes per second). In still another example, the second data transfer rate can be about 1 Bps (1 byte per second). In some embodiments, depending on the frequency of events or lack of events, the transfer rate can be scaled down even further.

It should be understood that these example rates, parameters, and/or sizes can change over time, depending on standards, customizations, and/or optimizations. So therefore, these parameters should only be viewed as examples. It is further understood that the methods and devices defined herein can implement embodiments that include more than two data transfer rates. In fact, the number of data transfer rates can include any number, based on a number of predefined scaled up or scaled down connection intervals. The number of intervals will vary, of course, depending on the implementation.

By scaling the connection intervals up or down, it is not the actual throughput that is being changed, but rather the possible bandwidth that can be supported by the channel. In the first data transfer rate, the scaled setting uses almost all of the channel bandwidth. In the second data transfer rate, most of the available channel bandwidth goes unused. A consideration for both transfer rates is latency, so the system does not want to have to wait too long before a single event (e.g., essentially one bit of information) can go from one device to another.

Returning to FIG. 4A, activity begins in operation 402 where the activity tracking device detects and stores activity data associated with motion or data collected by the device. In the example of FIG. 4A, it is assumed that the activity tracking device has never been synchronized a website (e.g., site) of a server. Therefore, a pairing of the activity tracking device to the site needs to occur, at least once.

The client device, in operation 408 may detect that an application is opened on the client device. The application that is opened is the activity tracking application 202, for example. In operation 410, the client device begins to pair with the activity tracking device. Pairing may occur, for example, upon request of a user that initiates the pairing.

The pairing, in this embodiment is a pairing between the activity tracking device and the site, which is enabled via the computing device client. For example, the scanning, connecting and data transfer at the computing device will enable the pairing with the site. If the activity tracking device has activity data, it will also be synchronized with the site, as shown in 424 and 425. The communication between the computing device and the activity tracking device is carried out in accordance with the first transfer rate, which uses a scaled-up connection interval to transfer data. The first transfer rate can include, for example, command data 430 requesting data from the activity tracking device, sending data 432, and acknowledgement information 434 for received data. At this point, the user may wish to close application 414 at the client computing device.

In FIG. 4B, an example is shown of a connection where the activity tracking device had previously been paired to the site on the server, in accordance with one embodiment of the present invention. In operation 402, activity data is detected and stored on the activity tracking device. At some point, an application is opened 408 at the computing device. As noted above, the application may be an activity tracking application 202. An update condition is detected by the client device, which is identified by opening the application. The update condition will act to scale-up the connection interval, so as to set a first data transfer rate.

The thick arrows 430, 432 and 434 represent the first data transfer rate, which is a faster transfer rate than the second transfer rate. Once the syncing with the site 404 and sync 425 is complete, using the scanning, connecting and data transfer 412 of the client, the operation of real-time client display updates 406 is processed.

The update condition has now changed, which causes a scale down of the connection intervals between the activity tracking device and the computing device. This, as noted above, causes the second transfer rate to govern for data exchanged to the computing device for real-time data display. In one embodiment, arrow 436 indicates a request from the computing device for real time updates. Arrows 438 indicate data transfers of any data available for transfer, using the second data transfer rate. Arrow 439 indicate a command that the client device has closed the application 414, so that the device can stop sending updates.

FIG. 4C illustrates an embodiment where the activity tracking device is connected to the computing device, without a connection with the server. Without server connection, the computing device (client) will not establish a pairing with the server, but instead will only establish a connection with the activity tracking device to perform real-time client display updates. As noted above, the activity tracking device will be set to communicate with the computing device using the second transfer rate, which is a result of scaling down the connection interval for performing the transfer of updates.

In this embodiment, the transfer of updates takes place to the computing device, which can display updates from the tracker in substantial real time. In one embodiment, the updates are transferred at a rate that is substantially not noticeable to a user viewing a changing screen or display of the computing device (e.g., the display of a smartphone, a smart watch, glasses device, etc.). In one example, the substantial real-time updates occur with transfer delay to the display that is less than about 2 seconds. In other embodiments, the transfer delay is less than about 1 second. In still other embodiments, the transfer delay is less than about 0.6 second. To human perception, the updates would appear to occur in real-time, wherein the updated activity data is continuously updated to the client device, and the display changes continuously or intermittently, depending on whether activity was captured or not. In some embodiments, the real time display will show numbers on a screen changing, such as counting steps, counting stairs, showing distance traveled, etc.

The communication between the client device and the server is executed using an Internet connection link, such as a Wi-Fi connection or cellular connection. As noted in this disclosure, the activity tracking device can be a wearable device on the wrist of a user, or a device that can be held by the user or attached to the user's clothing. As the user engages in motion or activities, the captured information can be transferred directly to the client device, such as a smart phone having an activity tracking application 202.

If the activity tracking application 202 is open, and the user is viewing one or more screens or data provided by the activity tracking application, that motion or activity data is transferred to the smart phone for display. Thus, if the user is currently viewing a screen that displays metric data associated with the activity being performed by the user, that activity can be updated substantially in real time as the user engages in the activity. For example, if the user is walking while viewing the screen that displays the number of steps, the number of steps can be shown to increase as the user is walking and viewing the display on the smart phone.

As the flow diagrams of FIGS. 4A-4C show, communication is managed between activity tracking device, the computing device, and the backend server. However, it should be understood that the communication between the activity tracking device and the client device can occur without having any Internet connection or connections to the backend server, as noted with response to FIG. 4C. When Internet connection is established by the client device at some point, the client device can then synchronize with the backend server, such as during background syncs, or when the app on the client device is again opened.

FIG. 5 is a diagram 500 illustrating the dynamic switching between first connection interval settings 502 and second connection interval settings 504, in accordance with one embodiment of the present invention. In this example, the vertical axis is the transfer rate, while the horizontal axis is time. At some point in time, an application is opened at a client device. The application that is opened is, in one example, an activity tracking application 202, as described in FIG. 3. When the activity tracking application 202 is opened, the communication between activity tracking device and the client device will be scaled up in terms of the connection interval. The connection interval defines a first transfer rate 506 where packets are sent during a period of time, or the frequency.

As mentioned above, the first connection interval setting 502 may transfer one packet every about 10 ms to about 30 ms. The packet transfer occurs over a low-energy Bluetooth connection, which saves energy by the activity tracking device. In one embodiment, the first connection interval setting 502 will remain during the data transfer. The data transfer that occurs upon first opening the application 202 is to transfer data that has been stored in the activity tracking device for some time. This data may include data held by the activity tracking device for several hours, days, or even months.

Therefore, during the first connection interval setting 502, such collected and stored data is downloaded to the client device so as to enable the client device to process the data and display information on one or more graphical user interfaces of the activity tracking application 202. In one embodiment, the first connection interval setting 502 can also be used to transfer firmware from the client device to the activity tracking device.

The transfer of firmware to the activity tracking device generally includes transferring a larger chunk of data, and the increased or scaled up connection interval allows for such transfer to occur at a relatively fast rate. By using a scaled up connection interval, over a Bluetooth low-energy connection, the scaled-up connection interval provides for essentially a serialized transmission channel between the client device and the activity tracking device. In Bluetooth low-energy, serial data transfers are not allowed, but by scaling up the connection interval, it is possible to simulate an actual serial connection. In the context of firmware updates, it is noted that the firmware image is running on the activity tracking device, so updates need to be coordinated with the transmission of commands to save state, stop running the image, install the image, and resume execution of the firmware image update. Because the connection between the activity tracking device and the client devices is essentially serialized (due to the scaled up connection interval setting), the firmware image files and commands to update can be managed by the server.

The server, when it is determined that updates are needed, can issue instructions to scale up the connection interval, transfer the firmware updates and coordinate the install, directly from the server. In one embodiment, by coordinating the firmware update from the server, it is not necessary to have the application running on the client device manage the updates, which also avoids having to coordinate with App stores and sites to enable firmware updates. The determination to update, the updating, and the coordination of the updates can be directed from the server, at any schedule or when updates are needed. In this configuration, the client device simply acts as a communication pipe that enables the direct communication and exchange of control and data/firmware to the activity tracking device from the server.

In one embodiment, a device 100 can have two operating systems (OSs) so that each can be updated independently, and without risk of leaving device unable to communicate over Bluetooth. In one configuration, the firmware update protocol includes deciding which OS the tracker will boot. The site on the server stores information about every firmware version and can compute deltas and data migration instructions from any version to any other version. For example, the computing device client can iteratively query current state from device 100, send the state to the site, receives in response a particular command to send to the device, and then after executing the command again queries the device for its current state. In this manner, no details about any particular version needs to be known by the client, as the site can manage the firmware updates.

Continuing with FIG. 5, at point 512, it is detected that the download of data has concluded or the firmware update has concluded, and at that point the connection interval is scaled down to a second connection interval setting 504. The second connection interval setting 504 acts to reduce the transfer rate to a second transfer rate. As noted above, the second transfer rate is used because the amount of data being transferred during this time only represents updates to data stored in the client device. For example, the updated data can include currently monitored step count, which is transferred as small packet updates to the client device.

The client device can then display in substantial real-time the updates on one or more of the graphical user interface screens provided by the activity tracking application 202. As noted above, one example of the second transfer rate can be to transfer one packet every 500 ms. This transfer rate is sufficient to update one or more of the metrics being captured by the activity tracking device and configured for display in substantial real-time on the client device (screen of a smart phone). The second connection interval setting 504 will remain during the period of time when updates for changes in activity data are captured by the activity tracking device or data is ready for transfer. When the activity tracking application 202 closes, the substantial real-time updates will stop or terminate.

FIG. 6 illustrates a graph 550 showing various periods of time when transfers occur between the activity tracking device and the client device, in accordance with one embodiment of the present invention. In the example, data transfers (e.g., updates) occur during background updates 602, download updates 604, real-time updates 606, and no updates during out of range computing devices 608. In this example, the first transfer rate 506 and the second transfer rate 508 are shown in the vertical axis. The horizontal axis displays time.

When the activity tracking application 202 is not open, but the computing device is within a range of communication with the activity tracking device, background updates 602 are enabled. Background updates are programmed at predetermined times depending on how often or how infrequent updates have been received from an activity tracking device. In the graph, background updates occurred at times t1-t2, t3-t4, and t5-t6. In one embodiment, background syncing can be triggered by the tracker advertising that it has data to sync and typically the real world time between these data syncs is 15-90 minutes, or typically occurring in the 20-30 minute range. Background mode updates/syncing, however, is enabled when the activity tracking device is within communication range of the computing device (client device). In one embodiment, the range can be defined by capabilities of low-energy Bluetooth standards, and also taking into consideration the environment and/or structures between the tracker and the client.

In other embodiments, other communication distances may be enabled if other wireless standards are used now or in the future. As further shown, the background update 602, in one embodiment occur at the second transfer rate 502, which implement the second connection interval setting. In an alternate embodiment, the background update 602 can be performed using the first interval connection setting 502. Download updates 604 occur at the first connection interval setting, where larger chunks of data are transferred from storage of the activity tracking device when it is detected that the application has opened at time t7. Between time t7 and t8, the download updates 604 occur, or firmware updates to the activity tracking device.

The transfer rate is set at the first transfer rate by scaling up the connection interval between the activity tracking device and the computing device (transferring at the first connection interval setting 502). After it is detected that the application has closed at time t8, the second connection interval setting 504 is set by scaling down the connection interval. This places real-time updates 606 at the second transfer rate 508. As illustrated by the vertical bars, transfers are less continuous during this time, and depend on whether or not data is being produced by the activity tracking device and there is a need to transfer the data to the client device. For any such transfers of data, the transfers will occur at the second transfer rate, dictated by the second connection interval setting 504. At time t9, it is determined that the application has closed. If the computing device goes out of range of the activity tracking device, no updates will occur during time 608.

Figure 7:
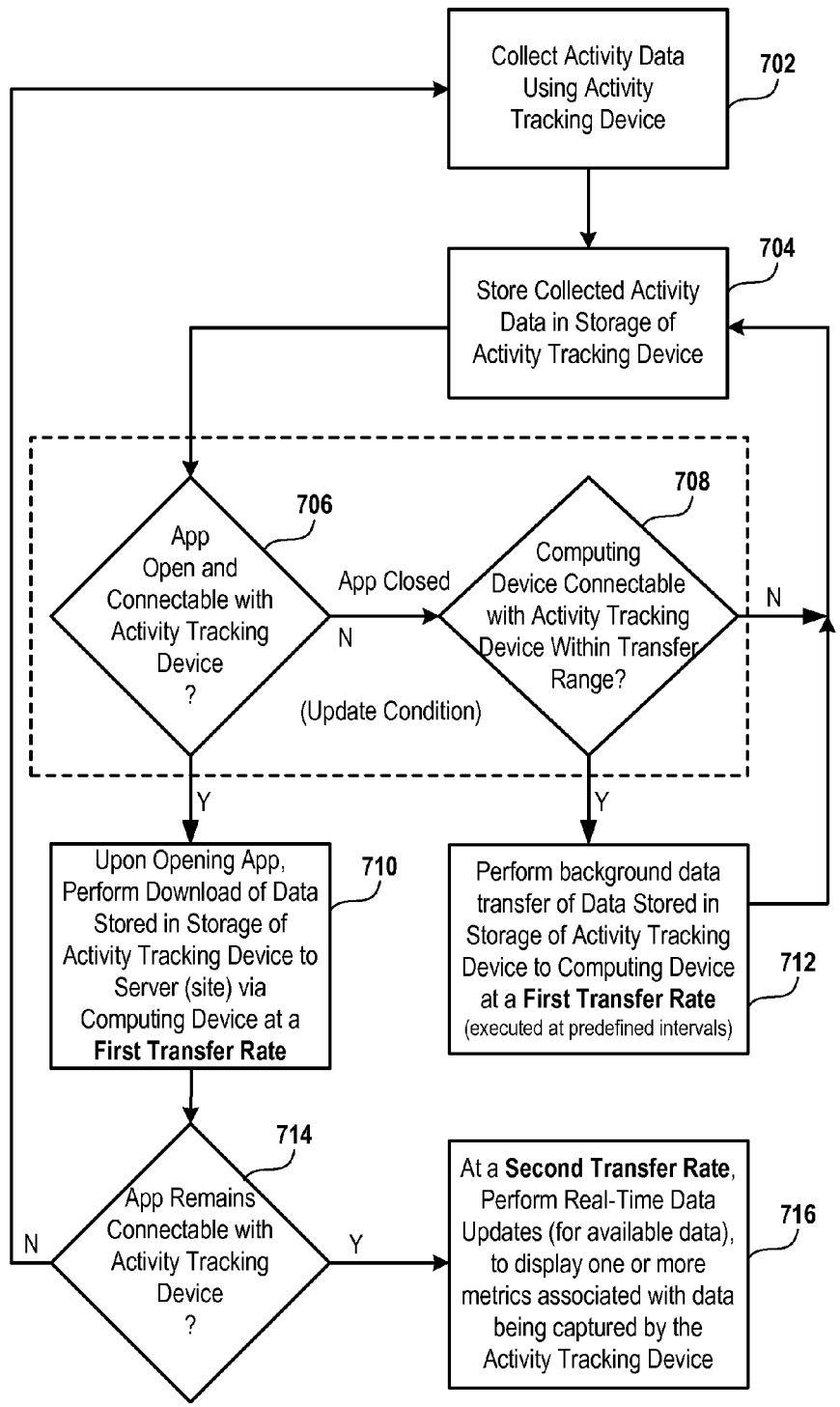
FIG. 7 illustrates a flowchart diagram associated with one embodiment of the present invention where the connection interval is scaled up or down depending on update condition detected between the activity tracking device and the computing device (client device).

FIG. 7 illustrates a flowchart diagram associated with one embodiment of the present invention where the connection interval is scaled up or down depending on update condition detected between the activity tracking device and the computing device (client device). The method begins in operation 702 where activity data is collected using the activity tracking device. The activity data is a result of motion data produced by the user who is wearing, holding, or carrying connectivity tracking device. The activity data can also be associated with data monitored by the device, such as blood pressure, heart rate, barometer reading, and other metrics associated with environmental conditions or conditions of a user. In operation 704, the collected activity data is stored in storage of the activity tracking device. The storage can be any type of memory, such as nonvolatile memory.

The update condition is determined at operation 706 and 708, in one example. For instance, in operation 706 it is determined if the application (e.g., activity tracking application 202) is open and is connectable (e.g., within range for connection) with the activity tracking device. If the application is not opened, it is determined in operation 708 if the computing device is connectable with the device within a transfer range. If the computing devices is within a transfer range, the method moves to operation 712. In operation 712, a background data transfers performed to the computing device using the second transfer rate, which is at a pre-defined scaled interval connection speed.

In another embodiment, background transfers can be executed at the first transfer rate. If it is determined that the device is not within the range of transfer with the computing device in operation 708, the method returns to operation 702 where that activity tracking device continues to collect data. If it is determined in operation 706 that the application is open and is within the transfer range, the method moves to operation 710 where a download of data stored in the storage of the activity tracking device is transferred to the computing device at the first transfer rate. As noted above, the first transfer rate is faster than the second transfer rate, and is designed to transfer larger amounts of data over a low-energy Bluetooth wireless connection.

The first transfer rate may be, for example, enabling the transfer of a packet every 10 ms to 30 ms, whereas the second transfer rate may be enabling transfer of a packet after more than 200 ms, or after more than 300 ms, or after 400 ms, or after 500 ms. In operation 714, it is determined that the application is connected with the activity tracking device and is open. If the application remains open, then real-time updates 716 are performed such that one or more metrics associated with collected activity data is transferred to the computing device from the activity tracking device. This information can be displayed in substantial real time on one or more screens of the activity tracking application 202 rendered on a computing device 200 (e.g. smart phone, tablet, etc.). If in operation 714 it is determined that the application is no longer open, the method would return back to 702 where the activity tracking device continues to track data and store it in operation 704.

Figure 8:
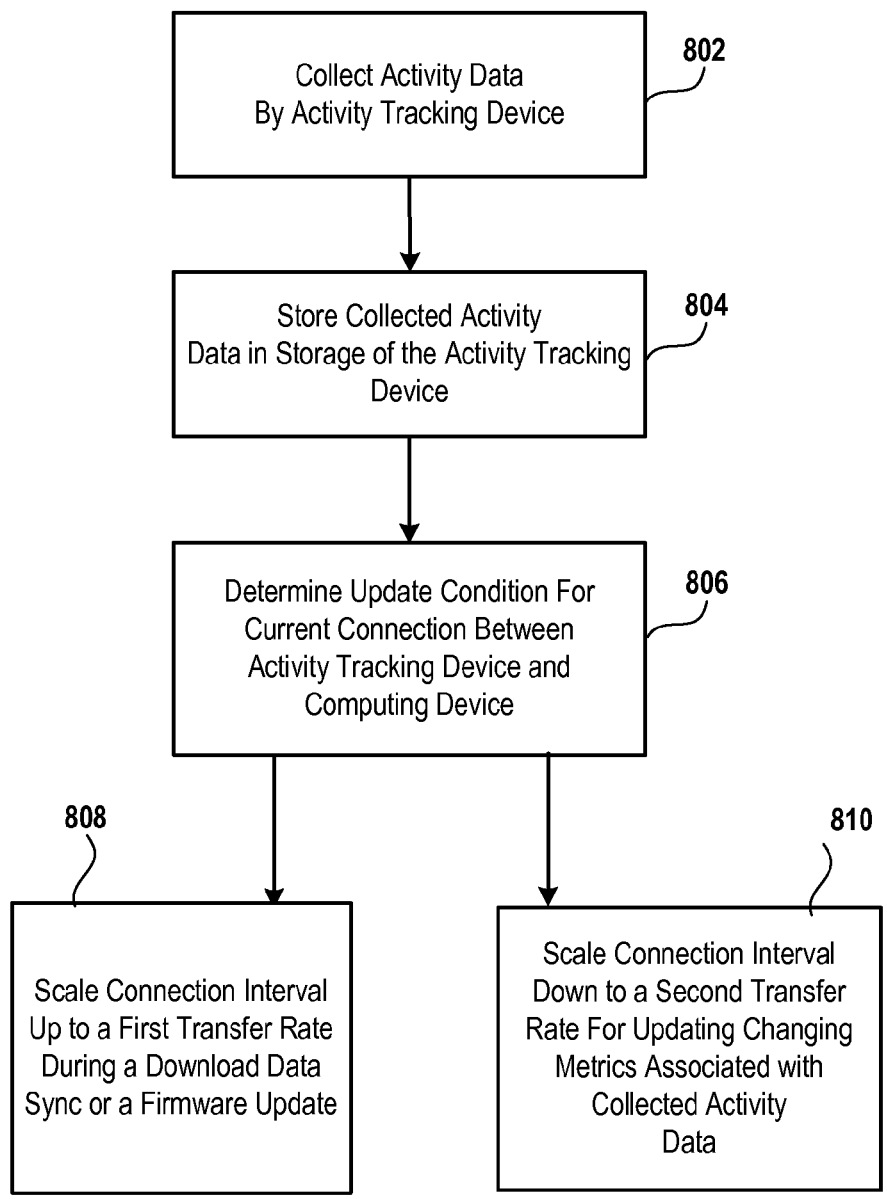
FIG. 8 illustrates a flowchart diagram of one embodiment of the present invention.

FIG. 8 illustrates a flowchart diagram of one embodiment of the present invention. In this example, operation 802 includes collecting activity data by the activity tracking device. As noted above, the type of data collected by the activity tracking device can be associated with motion data, data monitored from the user, data monitored from surrounding conditions, etc. In operation 804, the collected activity data is stored in storage of the activity tracking device.

In operation 806, the update condition is determined for a current connection between the activity tracking device and a computing device. The update condition can identify whether an application has just been opened, whether the application remains open after a first transfer rate has concluded to transfer stored data or perform firmware updates, or if background updates are required. Depending on the update condition, it is determined whether to scale the connection interval up or down to optimize the data transfer operation. In operation 808 it is determined that the connection interval should be scaled up to a first transfer rate during a download of data from the activity tracking device to the client device, or a firmware update from the client device to the activity tracking device.

In operation 810, it is determined that the connection interval should be scaled down to a second transfer rate for updating changes to metrics associated with collected activity data. At the scaled down connection interval rate, e.g., the second transfer rate, updates associated with one or more metrics can be transferred to the client device for display on one or more graphical user interface screens. The graphical user interface screens can include metric data that is changing on the fly as the user generates activity.

For instance, if the user is walking while viewing the one or more graphical user interface screens of the client device (e.g. running the activity tracking application 202), the step count will be shown to be increasing as the user takes each step. In another example, if the user is climbing stairs, the stair account would be increasing. In still another example, if the user is producing very active motion, the count of very active minutes can be shown to increase dynamically. Similarly, the calories burned count can be shown to increase dynamically while the user is performing an activity.

In one embodiment, synchronization (e.g., syncing) is a process between an activity tracking device and the web site. For example, the client device can be viewed as a dumb pipe that merely transmits data to the web site and then transmits a response to the activity tracking device. If there is no internet connection for the client device, no syncing is performed with the website. Syncing can then occur at a later time when an Internet connection has been established. In one embodiment, a "store and forward" type of approach can be implemented which just introduces asynchronous delays. The client would retrieve data from the tracker when it could, store it, and then relay the data to the site and get a response from the site later when there was an internet connection. In one embodiment, later, when the tracker was again available, the client could send the stored response to the tracker.

In some embodiments, a device is provided. The device is defined in a form of a wearable wrist attachable structure. In one embodiment, the device has a housing that is at least partially constructed or formed from a plastic material. In one embodiment, the housing of the device includes an altimeter. The defines can further include a transiently visible display, or a dead-front display, a touch screen display, a monochrome display, a digital display, a color display, or combination thereof. In yet another embodiment, the device can include one or more accelerometers. In one specific example, the device can include a 3-axis accelerometer. On still another embodiment, a 3-axis accelerometer can be replaced with or replicated by use of separate accelerometers (e.g., 3 accelerometers) positioned orthogonally to each other.

Figure 9:
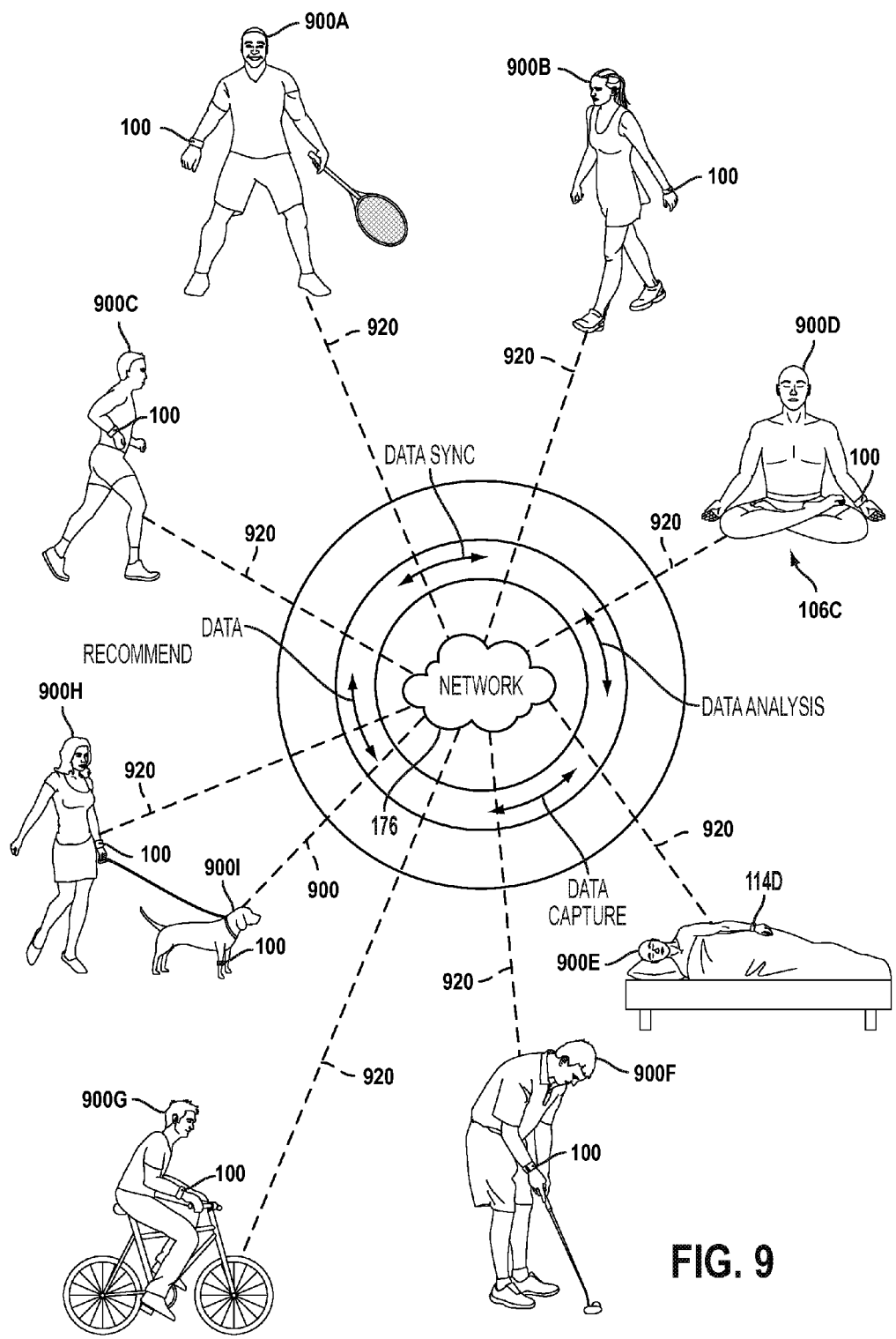
FIG. 9 illustrates an example where various types of activities of users can be captured or collected by activity tracking devices, in accordance with various embodiments of the present invention.

FIG. 9 illustrates an example where various types of activities of users 900A-900I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 920 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the user's smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method, comprising,
capturing activity data associated with activity of a user via a device, the activity data being captured over time, the activity data quantified by a plurality of metrics;
storing the activity data in storage of the device;
connecting the device with a computing device over a wireless communication link;
detecting an update condition when the device is connected with the computing device; and
setting a packet transfer rate between the device and the computing device based upon the detected update condition, the update condition used to select one of a first transfer rate for transferring activity data captured and stored over a period of time or a second transfer rate for transferring activity data that is displayable in substantial-real time on the computing device;
wherein the update condition is used to select the first transfer rate when detecting a starting of an activity tracking application on the computing device;
wherein the update condition is used to select the second transfer rate while the device is connected with the computing device and the activity tracking application is open, the method is executed by a processor.

2. The method of claim 1, wherein the first transfer rate is selected for transferring the activity data from the storage of the device to the computing device.

3. The method of claim 1, further comprising,
transferring the activity data to an activity management server to update the plurality of metrics associated with the activity of the user, the activity management server, from time to time, synchronizing activity data and settings with the computing device.

4. The method of claim 1, wherein the second transfer rate is selected to transfer activity data, upon or substantially after being produced in the device, to the computing device for display on the computing device in substantial real-time.

5. The method of claim 1, wherein the first transfer rate is set at a scaled-up connection interval, while the second transfer rate is set at a scaled-down connection interval, the first transfer rate being higher than the second transfer rate.

6. The method of claim 1, further comprising,
detecting the device being within a proximity distance from the computing device, the proximity distance being within a Bluetooth wireless communication distance; and
enabling connection.

7. The method of claim 6, wherein the update condition further determines that the device is connectable with the computing device and the activity tracking application closed, and enabling the second transfer rate for processing background transfers of activity data from the device to the computing device, the background transfers occurring at predefined intervals and the tracking application remains closed and is installed on the computing device.

8. The method of claim 1, further comprising,
receiving setting configurations from the activity management server, as obtained from the computing device, the setting configurations being received from a user account that is associated with the device, the activity management server configured to render graphical user interfaces on a website to display the plurality of metrics in various illustration configurations, the transferring of the activity data in the first transfer rate and the second transfer rate acting to obtain activity data from the device and synchronize the plurality of metrics for display on the computing device and on the website.

9. The method of claim 1, wherein the first transfer rate enables transfer of firmware updates to the device, in response to installation commands obtained from a server.

10. The method of claim 6, wherein the plurality of metrics include a time of day metric and metrics representing activity data captured by the device or sensed by the device.

11. The method of claim 1, wherein the plurality of metrics include one or more of step count metrics, or stair count metrics, or distance traveled metrics, or active time metrics, or calories burned metrics, or heart rate metrics, or sleep metrics, or combinations two or more thereof.

12. A device configured for capture of activity for a user, comprising,
a housing;
a sensor disposed in the housing to capture activity data associated with activity of the user, the activity data being captured over time, the activity data quantified by a plurality of metrics associated;
a memory for storing the captured activity data; and
a processor for managing connection of the device to a computing device over a wireless communication link, the processor detecting an update condition when the device is connected with the computing device, such that the processor sets a data transfer rate between the device and the computing device based upon the detected update condition, the update condition used to select one of a first transfer rate for transferring activity data captured and stored over a period of time or a second transfer rate for transferring activity data for display in substantial-real time on the computing device, the update condition is used to select the first transfer rate when an activity tracking application is opened on the computing device, and used to select the second transfer rate while the device is connectable with the computing device and the activity tracking application remains open.

13. The device of claim 12, wherein the housing is part of a wearable wrist attachable structure, or an attachable structure that can be carried or worn by the user.

14. The device of claim 12, further comprising one or both of an altimeter and an accelerometer.

15. The device of claim 12, wherein the housing further includes wireless communication logic for transferring data over the wireless communication link.

16. The device of claim 15, wherein the wireless communication logic includes one of WiFi processing logic, or Bluetooth (BT) processing logic, or radio processing logic.

17. The device of claim 16, wherein the computing device is configured for access with an activity management server over the Internet that receives the activity data of the device.

18. The device of claim 12, wherein the first transfer rate is selected for transferring the activity data from the storage of the device to the computing device, or firmware updates from the computing device to the storage of the device.

19. The device of claim 12, wherein the processor is configured such that the second transfer rate is selected to transfer activity data, upon being produced in the device, to the computing device for display on the computing device, in substantial real-time.

20. The device of claim 12, wherein the processor is configured such that
the first transfer rate is set at a scaled-up connection interval, while the second transfer rate is set at a scaled-down connection interval, the first transfer rate being higher than the second transfer rate.

21. The device of claim 12, wherein the processor is configured such that detection of the device within a proximity distance from the computing device is performed, the proximity distance being within a Bluetooth wireless communication distance; and
the processor is configured to then enable the connection.

22. The device of claim 21, wherein the processor, in response to analysis of the update condition, further determines,
that the device is connected with the computing device and the activity tracking application is closed, and
enables the second transfer rate for processing background transfers of activity data from the device to the computing device, the background transfers occurring a predefined intervals while the device remains connectable with the computing device and the tracking application remains closed and is installed on the computing device.

23. The device of claim 12, wherein the processor, in first transfer rate, enables transfer of firmware updates to the device, as directed by a server application.

24. A method, comprising,
capturing activity data associated with activity of a user via a device, the activity data being captured over time, the activity data quantified by a plurality of metrics and storing the activity data in storage of the device;
connecting the device to a computing device over a wireless communication link;
setting a data transfer rate between the device and the computing device based upon the detected update condition, the update condition used to select one of a first transfer rate for transferring activity data captured and stored over a period of time or a second transfer rate for transferring activity data that is displayable in substantial-real time on the computing device, the update condition is used to select the first transfer rate when it is detected that an activity tracking application is opened on the computing device, and the update condition is further used to select the second transfer rate while the device is connectable with the computing device and the activity tracking application remains open; and
transferring the activity data from the device to the computing device at the selected first or second transfer rate;
wherein the first transfer rate is set in response to scaling-up a connection interval and the second transfer rate is set in response to scaling-down the connection interval, the method is executed by a processor.

25. The method of claim 24, wherein the second transfer rate is selected to transfer activity data, upon or substantially after being produced in the device, to the computing device for display on the computing device, in substantial real-time.

26. The method of claim 25, wherein substantial real-time includes a delay of less than 1 second from a time at which activity data is produced on the device to being displayed on the computing device.

27. The method of claim 25, wherein the first transfer rate enables transfer of firmware updates to the device.

28. The method of claim 25, wherein the plurality of metrics include a time of day metric and metrics representing activity data captured by the device, measured by the device or sensed by the device.

29. A computer readable medium for storing program instructions executable by a processor, the computer readable medium comprising,
program instructions for capturing activity data associated with activity of a user via a device, the activity data being captured over time, the activity data quantified by a plurality of metrics, and storing the activity data in storage of the device;

program instructions for connecting the device to a computing device over a wireless communication link;

program instructions for setting a data transfer rate between the device and the computing device based upon the detected update condition, the update condition used to select one of a first transfer rate for transferring activity data captured and stored over a period of time or a second transfer rate for transferring activity data that is displayable in substantial-real time on the computing device, the update condition is used to select the first transfer rate when it is detected that an activity tracking application is opened on the computing device, and the update condition is further used to select the second transfer rate while the device is connectable with the computing device and the activity tracking application remains open; and program instructions for transferring the activity data from the device to the computing device at the selected first or second transfer rate;

wherein the first transfer rate is set in response to scaling-up a connection interval and the second transfer rate is set in response to scaling-down the connection interval.

30. The computer readable medium of claim 29, wherein the second transfer rate is selected to transfer activity data, upon or substantially after being produced in the device, to the computing device for display on the computing device, in substantial real-time, and the plurality of metrics include a time of day metric and metrics representing activity data captured by the device, measured by the device or sensed by the device.

\* \* \* \* \*